(12) United States Patent
Fishman (10) Patent No.: US 7,829,069 B2
(45) Date of Patent: Nov. 9, 2010

(54) HAIR TREATMENT SYSTEMS AND METHODS

(76) Inventor: Yoram Fishman, 3300 Wonderview Plz., Los Angeles, CA (US) 90068

( * ) Notice: Subject to any disclaimer, the term of this patent is extended or adjusted under 35 U.S.C. 154(b) by 1021 days.

(21) Appl. No.: 10/271,380

(22) Filed: Oct. 15, 2002

(65) Prior Publication Data

US 2004/0068805 A1  Apr. 15, 2004

(51) Int. Cl.
*A61K 8/00* (2006.01)
*A61K 8/02* (2006.01)
*A61K 8/18* (2006.01)
*A61K 8/64* (2006.01)

(52) U.S. Cl. .................. 424/70.1; 424/70.2; 424/70.5; 424/401

(58) Field of Classification Search .................. 424/70.1
See application file for complete search history.

(56) References Cited

U.S. PATENT DOCUMENTS

| | | | |
|---|---|---|---|
| 3,092,555 A * | 6/1963 | Horn | |
| 3,612,706 A | 10/1971 | Verga | |
| 3,973,853 A | 8/1976 | Myers | |
| 4,209,027 A * | 6/1980 | Morganroth | |
| 4,557,619 A | 12/1985 | DeVincentis | |
| 4,841,996 A | 6/1989 | Gueret | |
| 4,974,984 A | 12/1990 | Kafkis et al. | |
| 5,307,847 A | 5/1994 | Pavenick et al. | |
| 5,798,095 A * | 8/1998 | Racky | 424/70.19 |
| 6,050,271 A | 4/2000 | Spencer | |
| 6,325,070 B1 | 12/2001 | Tyroler et al. | |
| 6,334,449 B1 * | 1/2002 | Burrowes et al. | |

\* cited by examiner

*Primary Examiner*—Humera N Sheikh
(74) *Attorney, Agent, or Firm*—Konrad Raynes & Victor, LLP; Alan S. Raynes (57) ABSTRACT

A method for treating hair includes applying a first composition to the hair in a foam form and applying a second composition to the hair in foam form. The compositions are mixed on the hair. The first composition may include an oxidative dye. The second composition may include a oxidizing component such as hydrogen peroxide. An applicator for applying the compositions to the hair may take the form of a brush having a cavity thereon through which the foam compositions are delivered to the hair. A kit including the an aerosol container housing the oxidative dye, an aerosol container housing the oxidizing component, and a brush applicator may also be provided.

30 Claims, 4 Drawing Sheets

HAIR TREATMENT SYSTEMS AND METHODS

FIELD OF THE INVENTION

Preferred embodiments of the invention relate to hair treatment and includes hair coloring systems and methods for applying compositions to the hair.

RELATED ART

Hair treatment systems, for example, permanent hair dye systems, have commonly been comprised of a combination of a dye material and a developer or activator solution, most commonly hydrogen peroxide. Additive materials including thickeners, fillers and perfumes are sometimes included in the hair dye system.

Typically, the two parts of the system are packaged separately until use, when they are combined in one container, the container capped, and then shaken well to mix and activate the product. The mixing container may be used as an applicator by, for example, snipping off the tip of the bottle cap and carefully pouring the mixed liquid solution onto the roots of the hair and combing or working the solution into the hair by hand to thoroughly and completely saturate the hair. Alternatively, the mixing container may comprise a bowl, into which the components are mixed prior to application to the hair. Gloves should be worn to avoid stains on the hands and fingers since the hands are used to spread and distribute the color. The mixture is usually left on the hair for about 15 to 30 minutes, depending upon the shade and color depth desired. Finally, the remaining mixture is shampooed out of the hair and the hair is dried.

The process may be repeated if the colorant is not evenly distributed or not of sufficient intensity. Care must be taken to prevent run-offs onto clothing, furnishings, etc. Once the two solutions are mixed together, the mixture must be used within a relatively short time, such as one hour.

Such a conventional system has a variety of shortcomings including: (1) problems in mixing the components together; (2) the added time needed to prepare the working dye solution; (3) components wasted as one bottle is mixed with another and any excess is discarded; (4) difficulty in the control of the liquid application while applying the dye to hair; and (5) problems with applying the dye to hair on different locations in an even manner.

SUMMARY

Certain embodiments of the present invention relate to a method for applying a multi-component component system to the hair. The method includes applying a first component comprising a first foam to the hair. The method also includes applying a second component comprising a second foam on the hair after applying the first component to the hair, the second component having a different composition than the first component. The first component and the second component are mixed on the hair. In one aspect of certain embodiments, one of the first and second components comprises a colorant composition including, for example, an oxidative dye, and the other of the first and second components comprises a developer composition including, for example, hydrogen peroxide.

Embodiments also relate to a method for applying a hair colorant system to hair, including: forming a hair colorant concentrate comprising an oxidative dye and mixing the hair colorant concentrate with a propellant; placing the hair colorant concentrate with a propellant into a first pressurized container; forming a developer concentrate comprising an oxidizing agent and mixing the developer concentrate with a propellant; placing the developer concentrate with a propellant into a second pressurized container; delivering the hair colorant concentrate from the first pressurized container onto the hair in foam form and brushing the hair colorant concentrate through the hair using a brush coupled to the first pressurized container; and delivering the developer concentrate from the second pressurized container onto the hair in foam form and brushing the developer concentrate through the hair using a brush coupled to the second pressurized container; wherein the hair color concentrate and the developer concentrate are at least partially mixed on the hair as the hair is brushed.

Other embodiments relate to a hair treatment kit including a first component comprising a first concentrate and a propellant, the first component taking a foam form when delivered from a pressurized container to hair. The kit also includes a second component comprising a second concentrate and a propellant, the second component taking a foam form when delivered from a pressurized container to hair. The first concentrate has a composition different from that of the second concentrate. In one aspect of certain embodiments, the kit also includes an applicator for applying the components to the hair.

BRIEF DESCRIPTION OF THE DRAWINGS

Further objects, advantages and features of the present invention will become apparent from the detailed description, below, when read in conjunction with the accompanying drawings (which, for illustrative purposes, are not drawn to scale), which illustrate certain embodiments of the invention, where.

DETAILED DESCRIPTION OF PREFERRED EMBODIMENTS

It would be desirable to provide a system for applying products to the hair that overcomes one or more of the shortcomings described earlier, and which provides for an efficient and convenient application to the hair. Embodiments of the present invention are directed toward these and other objectives.

Certain embodiments of the present invention relate to and include compositions and methods for applying multi-component systems to hair. One example of such a system is hair dyes, including, for example, permanent hair dyes. One permanent hair dye embodiment includes a two component system including a color composition and a developer composition. These compositions each include a propellant therein and are housed in aerosol containers. The propellants are selected so that the color composition and the developer composition can be each applied to the hair as a foam. The aerosol containers may be selected so that an applicator can be positioned thereon, and the foam dispensed from the containers applied to the hair through the applicator. The applicator may in certain embodiments take the form of a brush having at least one cavity extending therethrough and with at least one opening in the bristle area of the brush through which the foam may be delivered to the hair. The first component, such as the colorant, is applied to the hair using the brush. Then the second component, such as the developer, is applied to the hair using the brush, with the components being mixed together on the hair while brushing.

Embodiments may also include kits containing multiple components and an applicator system packaged together. One such kit embodiment may include multiple bottles each having an aerosol valve thereon, packaged together with an applicator that is sized to fit onto the aerosol valves of the bottles.

Figure 1:
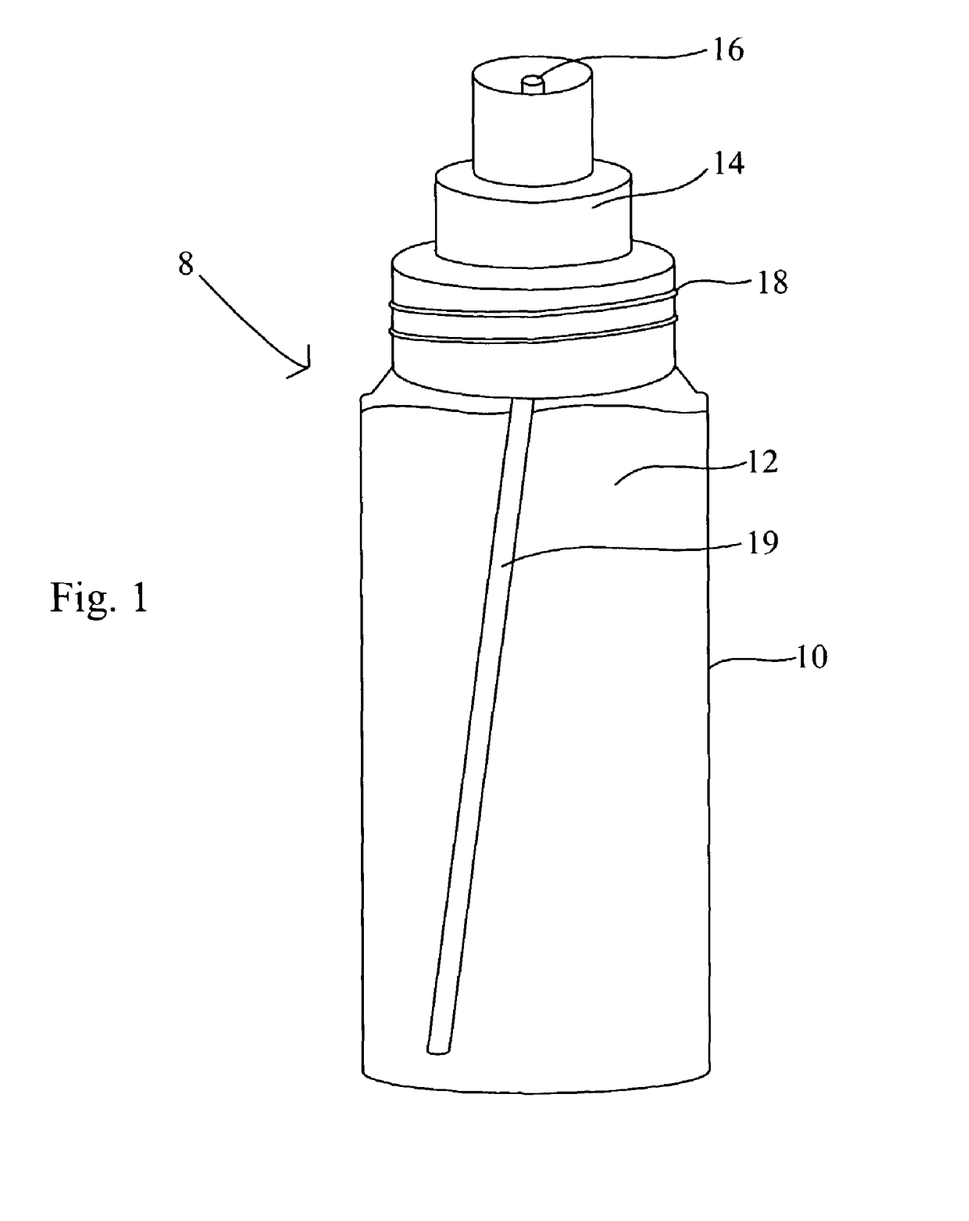
FIG. 1 shows a view of a bottle for holding various components according to certain embodiments of the present invention.

Certain embodiments will be discussed below with reference to FIGS. 1 through 4. As seen in FIG. 1, a container 8 including composition 12 therein is provided. The container 8 may include an aerosol can or bottle 10 and a valve housing 14 that is disposed on the top of the bottle 10. The valve housing 14 houses a valve 16 that is crimped onto the bottle 10. The exact type of bottle and valve used are not limited and any type of container as known in the art for materials such as pressurized liquids may be utilized. A tube 19 through which the composition 12 may flow may be provided in the bottle 10 and attached to the bottom of the valve 16.

For one hair coloring system embodiment, two such containers 8 may be used. One container houses a liquid hair coloring composition and a second container houses a liquid developer composition. The compositions include a propellant therein and are under pressure. Examples of colorant compositions and developer compositions will be set forth later.

Figure 2:
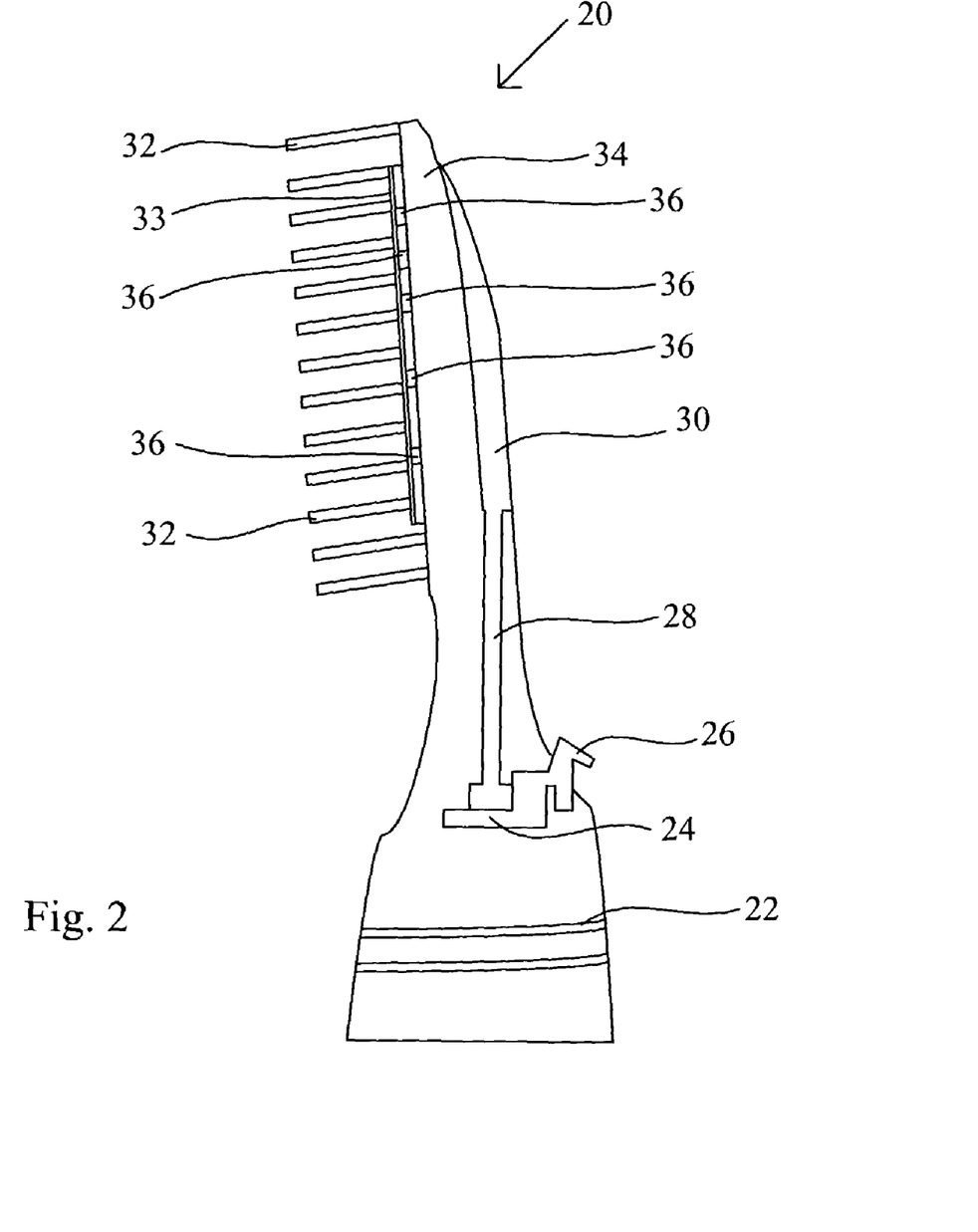
FIG. 2 shows a view of an applicator according to certain embodiments of the present invention.

FIG. 2 illustrates an example of an applicator to be used with the container 8 described above. The applicator 20 shown in FIG. 2 is in the form of a brush. The applicator 20 includes a lower screw-top region 22 sized to fit onto the region 18 on the housing 14 on the top of the bottle 10. The applicator 20 also includes an actuator which, as shown in FIG. 2, includes aerosol top fitting region 24 and actuator button 26. The aerosol top fitting region 24 fits over the valve 16 and is attached to actuator button 26. When the button 26 is pushed, the aerosol top fitting region 24 applies pressure to and actuates the valve 16 and the composition is delivered from the container 8 to the applicator 20. The actuator button 26 may be integral with or otherwise coupled to the aerosol top fitting region 24. The applicator 20 also includes a tube 28 attached to the aerosol top fitting region 24 and extending to a cavity 30 that extends up along the body region 34 of the applicator 20. The tube 28 may also be integral with or otherwise coupled to the aerosol top fitting region 24. The upper portion of the applicator 20 includes a plurality of bristles 32 extending outward from the body region 34. The cavity 30 connects through the body region 34 to tracks 39 (shown in FIG. 3) that lead to openings 36 (five openings are shown in FIG. 2) on the bristle side of the body region 34 through which the composition may flow.

Figure 3:
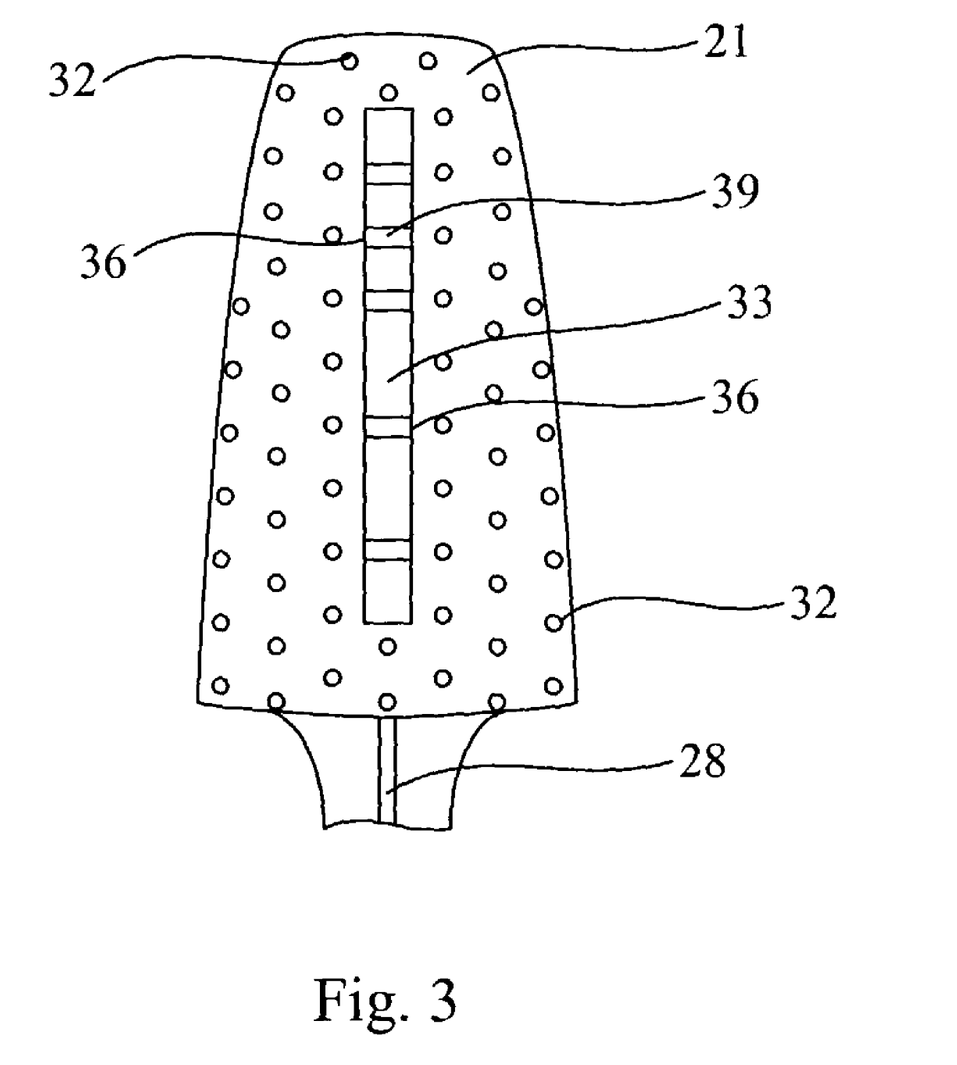
FIG. 3 shows a view of a portion of an applicator according to certain embodiments of the present invention.

FIG. 3 shows a view of the brush face 21 of the applicator 20 including the bristles 32 extending therefrom. The applicator 20 may be made from a variety of materials, including, for example, translucent or transparent polymers. FIG. 3 also shows cover 33 that covers tracks 39 (which are visible under the cover 33) that extend to the cavity 30 through the body region 34 (shown in FIG. 2). The openings 36 are positioned to open on either side of the tracks 39 on the sides and below the cover 33. FIG. 3 also shows a portion of the tube 28 extending up into the upper region of the applicator.

Figure 4:
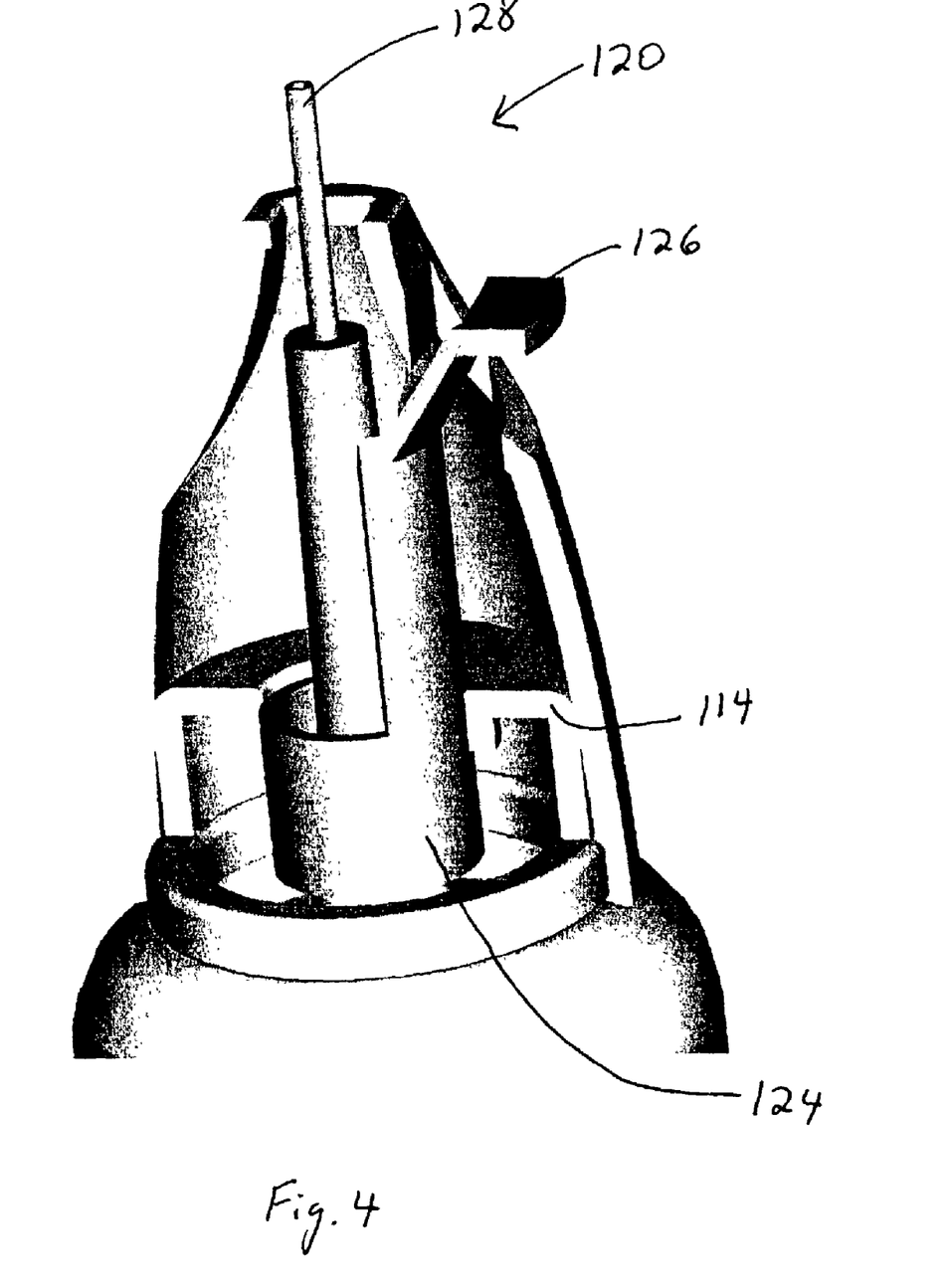
FIG. 4 shows a view of a portion of an applicator according to certain embodiments of the present invention.

FIG. 4 illustrates a detailed view of a portion of an applicator 120 embodiment similar to that described above. As seen in FIG. 4, the applicator 120 includes an aerosol top fitting region 124 that fits over a portion of the valve housing 114 of a bottle. The button 126 is attached to the aerosol top fitting region 124, and as the button 126 is pushed, the region 124 presses on and actuates the valve in the valve housing 114. The tube 128 extends from the aerosol top fitting region 124 to deliver the product to an upper portion (not shown in FIG. 4) of the applicator 120 which may include a brush having a cavity and openings similar to those shown in FIG. 2 for delivering the foam product to the hair.

In certain embodiments, both the hair coloring composition and the developer composition are formulated to have a foam consistency when delivered from the bottle through the applicator to the hair. The compositions are delivered to the hair through the action of applying the foam to the hair with the brush. In general, surface forces attract the bubbles together and the bubbles then collapse on the hair over time. The brushing action assists in the process of collapsing the bubbles and delivering the product to the hair. This permits a user to apply one of the compositions (for example, the color composition) to the hair in foam form, saturate the hair as needed while brushing the composition through the hair, and then apply the developer composition to the hair in foam form. The compositions may then be thoroughly mixed as needed on the hair as the brush is run though the hair. In certain embodiments the brushing action will eliminate most of the foam bubbles in the first few seconds of brushing, with up to about 10 brush strokes usually needed to fully saturate the hair. To obtain the desired color on the hair, the mixed product may be left on the hair for a time such as, for example, 15-30 minutes and then the hair may be washed to remove any remaining products.

Numerous oxidative dyes and dyeing agents may be used in the colorant compositions of preferred embodiments of the present invention, including, for example, aromatic phenols, polycyclic phenols, hydroxy benzene with substitute groups (ortho, meta, para) such as nitro, amino, amido, sulfo, chloro, bromo, and combinations thereof. Examples include, but are not limited to: para phenylenediamine; para phenylenediamine hydrochloride; para phenylenediamine sulfate, meta phenylenediamine sulfate; ortho, meta, para aminophenol; meta aminophenol sulfate; 2, 4, diaminophenetol sulfate; 5-amino 2-methylphenol; ortho, meta, and para nitrophenol; 2-nitro-P-phenylenediamine; 4-nitro-O-phenyleneidamine; para amino ortho cresol; ortho, meta, and para chlorophenol; the acid salts of the above phenols; alpha naphthol; 1,5-dihydroxynaphthalene; resorcinol and 4-chlororesorcinal. Numerous other dyes and pigments or color enhancing components may also be utilized if desired in compositions according to embodiments of the present invention including, for example, U.S. Government certified colors, both Drug and Cosmetic grade and Food, Drug and Cosmetic grade.

Numerous oxidizing agents may be used in the developer in embodiments of the present invention. For example, water soluble peroxides including hydrogen peroxide may be utilized. Other oxidizing agents which may be used include, for example, sodium peroxycarbonate, sodium perborate and urea peroxide.

As seen in Table 4 below, one example of a propellant which may be used in embodiments of the present invention is isobutane. When mixed with the colorant composition and with the developer compositions in accordance with certain embodiments, the resultant mixtures (in liquid form) may be housed in pressurized containers as known in the art for holding aerosol mixtures.

Other propellants as known in the art may also be used if desired. As stated above, the mixture preferably yields a foam when delivered from the pressurized container to the hair. Examples of other propellants which may be used include, but are not limited to N-butane, dimethyl ether, 1,1 difluoroethane (152a), propane and nitrogen. Preferred quantities of propellants range up to about 15 weight percent.

A variety of ingredients may be optionally included in the hair colorant and the developer compositions, in order to impart desirable characteristics to the hair. For example, embodiments may include additives such as, for example, humectants, moisturizers, proteins, vitamins, herbal extracts, color enhancers, plasticizers, color fixatives, etc. as known in the art. Such additives may be added to one or both of the colorant and the developer compositions.

A variety of developer compositions may be used in embodiments of the present invention. One example of a developer composition includes an oxidative dye (hydrogen peroxide) and is set forth in Table 1 below.

TABLE 1

Developer composition.

| concentrate ingredient | developer (wt %) |
|---|---|
| water | 71.5481 |
| hydrogen peroxide | 16.6474 |
| isobutane | 6.0000 |
| nonoxynol-10 | 3.2900 |
| decyl glucoside | 2.3500 |
| cetyl alcohol | 0.1175 |
| phosphoric acid | 0.0282 |
| tetrasodium EDTA | 0.0188 |
| total | 100.0000 |

A variety of colorant compositions may also be used. Examples of colorant compositions for achieving various colors according to certain embodiments of the present invention include those set forth in Tables 2 and 3 below. It should be noted that the tables set forth the weight percentages for the concentrate portion of the compositions. In certain embodiments, the concentrate is mixed with a propellant in an amount of 94 wt % concentrate and 6% propellant as set forth in Table 4 below.

TABLE 2

Ingredients in weight percent for dark brown, ebony, red brown and red auburn permanent hair dye concentrate colors (without propellant).

| concentrate ingredient | dark brown (wt %) | ebony (wt %) | red brown (wt %) | red auburn (wt %) |
|---|---|---|---|---|
| water | 37.4790 | 38.6000 | 37.2800 | 38.9400 |
| lauramide DEA | 2.0000 | 2.0000 | 2.0000 | 2.0000 |
| oleic acid | 15.0000 | 15.0000 | 15.0000 | 15.0000 |
| propylene glycol | 10.0000 | 10.0000 | 10.0000 | 10.0000 |
| hexylene glycol | 2.5000 | 2.5000 | 2.5000 | 2.5000 |
| tetrasodium EDTA | 0.1000 | 0.1000 | 0.1000 | 0.1000 |
| decyl glucoside | 7.0000 | 7.0000 | 7.0000 | 7.0000 |
| nonoxynol-10 | 10.5000 | 10.5000 | 10.5000 | 10.5000 |
| ammonium hydroxide (QS up to a pH of 10-10.5) | 2.0000 | 2.0000 | 2.0000 | 2.0000 |
| isopropyl alcohol | 10.0000 | 10.0000 | 10.0000 | 10.0000 |
| sodium sulfite | 0.2000 | 0.2000 | 0.2000 | 0.2000 |
| erythorbic acid | 0.2000 | 0.2000 | 0.2000 | 0.2000 |
| P-phenylenediamine | 0.8460 | 1.0400 | 0.6500 | — |
| M-aminophenol | 0.1460 | 0.0800 | 0.1000 | 0.0320 |
| resorcinol | 1.6850 | 0.1600 | 0.1000 | — |
| 4-chlororesorcinol | — | 0.3200 | 0.1600 | — |
| 2,4 diaminophenetol sulfate | — | 0.1800 | 0.0600 | 0.0040 |
| P-aminophenol | — | 0.1200 | 1.4000 | 0.6800 |
| alpha-naphthol | 0.1680 | — | — | — |
| N,N-Bis(2-hydroxyethyl)-PPD sulfate | 0.1760 | — | — | — |
| 1,5 dihydroxynaphthalene | — | — | 0.0500 | 0.0040 |
| 5-amino 2-methylphenol | — | — | 0.7000 | 0.8000 |
| HC Yellow #5 | — | — | — | 0.0400 |
| CONCENTRATE TOTAL | 100.0000 | 100.0000 | 100.0000 | 100.0000 |

TABLE 3

Ingredients in weight percent for blonde and golden blond permanent hair dye concentrate colors (not including propellant).

| concentrate ingredient | blonde (wt %) | golden blonde (wt %) |
|---|---|---|
| water | 39.8900 | 40.3380 |
| lauramide DEA | 2.0000 | 2.0000 |
| oleic acid | 15.0000 | 15.0000 |
| propylene glycol | 10.0000 | 10.0000 |
| hexylene glycol | 2.5000 | 2.5000 |
| tetrasodium EDTA | 0.1000 | 0.1000 |
| decyl glucoside | 7.0000 | 7.0000 |
| nonoxynol-10 | 10.5000 | 10.5000 |
| ammonium hydroxide (QS up to a pH of 10-10.5) | 2.0000 | 2.0000 |
| isopropyl alcohol | 10.0000 | 10.0000 |
| sodium sulfite | 0.2000 | 0.2000 |
| erythorbic acid | 0.2000 | 0.2000 |
| P-phenylenediamine | 0.1000 | 0.0360 |
| M-aminophenol | 0.1000 | 0.0400 |
| 4-chlororesorcinol | 0.0600 | 0.0360 |
| 2,4 diaminophenetol sulfate | — | 0.0020 |
| P-aminophenol | 0.3500 | 0.0060 |
| 5-amino 2-methylphenol | — | 0.0060 |
| 4-nitro-O-phenylenediamine | — | 0.0310 |
| 2-nitro-P-phenylenediamine | — | 0.0050 |
| CONCENTRATE TOTAL | 100.0000 | 100.0000 |

TABLE 4

Fill percentages of concentrate (such as the colors set forth in Tables 2 and 3) and propellant isobutane to be placed into a pressurized container.

| Component | wt % |
|---|---|
| concentrate | 94.00 |
| A-31 (isobutane) | 6.00 |
| TOTAL | 100.00 |

Examples of procedures for forming certain embodiments of a permanent hair dye concentrate and a developer concentrate are described as follows.

To prepare the hair dye composition, in a mixing tank, water, lauramide DEA, oleic acid, propylene glycol, hexylene glycol, tetrasodium EDTA, decyl glucoside, and nonoxynol-10 are mixed, with the product preferably mixed well as each ingredient is added. In a separate container, water, isopropyl alcohol erythorbic acid, sodium sulfite, and dyes are added, with the products mixed well to dissolve the dyes. The mixed product is added to the main mixing tank and mixed well. The pH is adjusted using ammonia solution (preferably to a pH value of 11-12.5, more preferably, 12-12.5) and the solution is mixed well.

To prepare the developer composition, in a mixing tank, water, cetyl alcohol, nonoxynol-10, decyl glucoside and tetrasodium EDTA are combined and heated to 75° C. and mixed to dissolve and emulsify the materials. The batch is then cooled to 40° C. and hydrogen peroxide is added and the batch is mixed well. The pH is then adjusted with phosphoric acid (preferably to a pH value of 3-4) and mixed well.

As stated above, the resultant concentrates are then each mixed with a propellant and placed in a pressurized container.

The ingredients described in the hair dye concentrate and developer concentrate may be characterized in certain aspects as follows. For example, lauremide DEA may act as a foam booster and viscosity increasing agent, oleic acid may act as a surfactant and a cleansing agent, propylene glycol and hexylene glycol may act as humectants, tetrasodium EDTA may act as a chelating agent, decyl glucoside may act as a surfactant and a cleansing agent, nonoxynol-10 may act as a surfactant and emulsifier, isopropyl alcohol acts as a solvent, erythorbic acid and sodium sulfite may act as antioxidants, hydrogen peroxide acts as an oxidizing agent.

It should be noted that the classification of ingredients in compositions such as cosmetics may be somewhat arbitrary. For example, propylene glycol may be classified as both a humectant and as a viscosity modifier. Consequently, for purposes of the descriptions herein, the components are characterized according to what is believed to be a useful role in providing the desired properties as used in compositions as described above.

One or more of the following advantages may also be present in certain embodiments of the present invention. (1) By mixing the compositions on the hair, the need for additional mixing containers and the associated mess therewith is eliminated. (2) The hands need not be used to mix the components together or to directly apply the products to the hair, as the brush is used for delivering the compositions to the hair. (3) The foam compositions can be applied to the entire head or to specific portions of the hair, as desired. (4) The user may vary the amount product delivered and/or mixing done on the hair to vary the color tone. (5) The process can be carried out quickly because the mixing is done on the hair, not in a separate container and then applied to the hair. (6) The containers are reusable because the colorant and the developer are in separate pressurized aerosol containers. Once the desired quantity is delivered to the hair, the container is closed. As the preferred containers and delivery system are part of a one way system (product travels out only), the unused products in the containers will not readily oxidize. In general, certain preferred embodiments allow for safe, convenient treatment of the hair without the need for gloves and without the mess associated with conventional hair dye systems.

It should be appreciated that many modifications to the embodiments described above may be made. For example, certain hair treatment systems may include more than two steps. Thus, certain embodiments may include more than two compositions which can be applied to the hair in a foam form.

Further, such systems may include treatments other than coloring the hair, for example, bleaching or straightening the hair.

In addition, the containers and the applicator may take a variety of forms in addition to those discussed earlier. Alternative applicator designs may include a comb, a pad, or other type of structure best suited for applying the foam composition(s) to the desired location. Furthermore, methods other than those described above may be used for applying compositions to the hair.

What is claimed is:

1. A method for applying a multi-component system to the hair, comprising:
    applying a first component comprising a first foam to the hair;
    applying a second component comprising a second foam on the hair after applying the first component to the hair, the second component having a different composition than the first component; and
    mixing the first component comprising the first foam and the second component comprising the second foam on the hair so that a chemical reaction takes place between the first component and the second component on the hair.

2. A method as in claim 1, further comprising applying the first component to the hair using an applicator so that a user's hands do not have direct contact with the first component.

3. A method as in claim 2, further comprising applying the second component to the hair using an applicator so that a user's hands do not have direct contact with the second foam.

4. A method as in claim 1, wherein one of the first component and the second component comprises a colorant composition, and the other of the first and second components comprises a developer composition.

5. A method as in claim 4, wherein the colorant composition comprises an oxidative hair dye, and the developer composition comprises an oxidizing agent.

6. A method as in claim 1, including providing an applicator including a first region comprising a cavity therein and a second region comprising a plurality of bristles and at least one opening in the second region, wherein the applying a first component comprising a first foam to the hair includes delivering the first foam through the cavity and out of the opening in the second region of the applicator.

7. A method as in claim 6, wherein the applying a second component comprising a second foam to the hair includes delivering the second foam through the cavity and out of the opening in the applicator.

8. A method as in claim 6, wherein the mixing the first component and the second component on the hair comprises brushing the hair.

9. A method as in claim 1,
    wherein the first component comprises a colorant housed in a first pressurized container including a valve, and wherein the applying a first component comprising a first foam to the hair comprises actuating the valve on the first pressurized container; and
    wherein the second component comprises a developer housed in a second pressurized container including a valve, and wherein the applying a second component comprising a second foam on the hair comprises actuating the valve on the second pressurized container.

10. A method as in claim 9, wherein an applicator including a cavity therein is provided, and wherein the applying a first component comprising a first foam to the hair includes delivering the first foam through the cavity in the applicator.

11. A method as in claim 10, wherein the applying a second component comprising a second foam to the hair includes delivering the second foam through the cavity in the applicator.

12. A method as in claim 10, wherein the applicator includes a brush region including a plurality of bristles and at least one opening in the brush region, and wherein the applying a first component comprising a first foam to the hair includes delivering the first foam through the cavity and through the at least one opening in the brush region, and then brushing the hair with the brush region.

13. A method as in claim 12, wherein the applying a second component comprising a second foam to the hair includes delivering the second foam through the cavity and through the at least one opening in the brush region, and then brushing the hair with the brush region.

14. A method as in claim 9, wherein the colorant comprises an oxidative dye and the developer comprises an oxidizing agent.

15. A method for applying a multi-component system to hair, comprising:
   delivering a colorant composition in a foam consistency to the hair, the colorant composition comprising an oxidative dye;
   after the delivering a colorant composition in a foam consistency to the hair, delivering a developer composition in a foam consistency to the hair, the developer composition comprising an oxidizing agent; and
   mixing the developer composition and the colorant composition on the hair so that the hair is colored, wherein the mixing is carried out on the hair while at least some of the colorant composition is in the foam consistency and at least some of the developer composition is in the foam consistency.

16. A method as in claim 15, wherein the colorant composition is housed in a first pressurized container including a valve, wherein the developer composition is housed in a second pressurized container including a valve, and wherein the delivering a colorant composition comprises actuating the valve on the first pressurized container, and the delivering a developer composition comprises actuating the valve on the second pressurized container.

17. A method as in claim 16, wherein the delivering a colorant composition further comprises transmitting the colorant composition through an applicator having a brush region and at least one opening extending through the applicator to the brush region, wherein as the valve is actuated, the colorant composition is delivered through the applicator and out of the at least one opening to the hair in a foam form.

18. A method as in claim 15, further comprising, after the mixing the developer composition and the colorant composition on the hair, waiting a period of time and then washing the hair.

19. A method for applying a multi-component system to hair, comprising:
   applying a first composition on the hair in a foam form from a first pressurized container, the first composition selected from one of a colorant composition and a developer composition;
   applying a second composition on the hair in a foam form from a second pressurized container after the applying the first composition on the hair, the second composition being the other of the colorant composition and the developer composition; and
   mixing the first composition and the second composition on the hair, wherein the first composition is applied on the hair prior to any mixing of the first composition and the second composition.

20. A method as in claim 19, wherein the colorant composition comprises an oxidative dye and the developer composition comprises a oxidizing agent.

21. A method as in claim 19,
   wherein the applying a first composition on the hair comprises coupling an applicator to the first pressurized container and transmitting the first composition through the applicator; and
   wherein the applying a second composition on the hair comprises removing the applicator from the first pressurized container and coupling the applicator to the second pressurized container and transmitting the second composition through the applicator.

22. A method as in claim 19, wherein the first pressurized container includes a propellant therein, and the second pressurized container includes a propellant therein.

23. A method as in claim 19, including providing an applicator including a first region comprising a cavity therein and a second region comprising a plurality of bristles and at least one opening in the second region, wherein the applying a first composition on the hair includes coupling the applicator to the first pressurized container and transmitting the first composition through the cavity and out of the opening in the second region of the applicator.

24. A method as in claim 23, wherein the applying a second composition on the hair includes decoupling the applicator from the first pressurized container and coupling the applicator to the second pressurized container and transmitting the second composition through the cavity and out of the opening in the applicator.

25. A method as in claim 24, wherein the mixing the first composition and the second composition on the hair comprises brushing the hair using the applicator.

26. A method as in claim 1, wherein the applying a first component comprising a first foam to the hair includes transmitting the first component from a first pressurized container to the hair, the first pressurized container including a propellant therein; and wherein the applying a second component to the hair comprises transmitting the second component from a second pressurized container to the hair, the second pressurized container including a propellant therein.

27. A method for applying a multi-component system to the hair, comprising:
   applying a first component comprising a first foam to the hair;
   applying a second component comprising a second foam on the hair after applying the first component to the hair;
   mixing the first component and the second component on the hair so that a chemical reaction takes place between the first component and the second component on the hair;
   wherein one of the first component and the second component comprises an oxidative hair dye, and the other of the first component and the second component comprises a oxidizing agent; and
   wherein the first component is applied to the hair prior to any mixing of the first component and the second component.

28. A method as in claim 27,
wherein the first component comprises a colorant housed in a first pressurized container including a valve, and wherein the applying a first component comprising a first foam to the hair comprises actuating the valve on the first pressurized container; and
wherein the second component comprises a developer housed in a second pressurized container including a valve, and wherein the applying a second component comprising a second foam on the hair comprises actuating the valve on the second pressurized container.

29. A method as in claim 19, wherein the mixing is carried out on the hair while at least some of the first composition is in the foam form and at least some of the second composition is in the foam form.

30. A method as in claim 15, wherein the first composition is delivered to the hair prior to any mixing of the first composition and the second composition.

\* \* \* \* \*